US008172764B2

(12) United States Patent
Gregson et al.

(10) Patent No.: US 8,172,764 B2
(45) Date of Patent: May 8, 2012

(54) METHOD AND SYSTEM FOR HIGH-RESOLUTION EXTRACTION OF QUASI-PERIODIC SIGNALS

(75) Inventors: Peter H. Gregson, Halifax (CA); Stephen Hankinson, Timberlea (CA)

(73) Assignee: Coeurmetrics Inc., Seabright, Nova Scotia (CA)

( * ) Notice: Subject to any disclaimer, the term of this patent is extended or adjusted under 35 U.S.C. 154(b) by 1047 days.

(21) Appl. No.: 12/091,536

(22) PCT Filed: Oct. 26, 2006

(86) PCT No.: PCT/CA2006/001751
§ 371 (c)(1),
(2), (4) Date: Apr. 25, 2008

(87) PCT Pub. No.: WO2007/048238
PCT Pub. Date: May 3, 2007

(65) Prior Publication Data
US 2008/0287819 A1    Nov. 20, 2008

(30) Foreign Application Priority Data
Oct. 26, 2005   (CA) .................................... 2524507

(51) Int. Cl.
*A61B 5/02*   (2006.01)
(52) U.S. Cl. ....................................................... 600/528
(58) Field of Classification Search .................. 600/483, 600/485, 500–503, 528
See application file for complete search history.

(56) References Cited

U.S. PATENT DOCUMENTS

| 4,905,706 | A | 3/1990 | Duff et al. |
|---|---|---|---|
| 5,109,863 | A | 5/1992 | Semmlow et al. |
| 5,159,932 | A | 11/1992 | Zanetti et al. |
| 5,584,295 | A | 12/1996 | Muller et al. |
| 5,825,657 | A | 10/1998 | Hernandez |
| 6,024,705 | A | 2/2000 | Schlager et al. |
| 6,572,560 | B1 | 6/2003 | Watrous et al. |
| 6,950,702 | B2 | 9/2005 | Sweeney |

FOREIGN PATENT DOCUMENTS
WO    2004/086967 A1    10/2004

OTHER PUBLICATIONS

International Search Report and Written Opinion for PCT/CA2006/001751 dated Feb. 15, 2007.

*Primary Examiner* — Mark W Bockelman
(74) *Attorney, Agent, or Firm* — Dinsmore & Shohl LLP (57) ABSTRACT

A quasi-periodic signal with high signal-to-noise ratio containing signal features that exhibit poor temporal localization is processed to identify waveform temporal reference points that are used to provide the temporal reference points for extracting a representative waveform of a signal feature having high temporal localization in a second, related, quasi-periodic signal that has low signal-to-noise ratio. The resulting representative waveform exhibits much improved signal-to-noise ratio while preserving the temporal detail contained in the second, related, quasi-periodic signal.

17 Claims, 8 Drawing Sheets

METHOD AND SYSTEM FOR HIGH-RESOLUTION EXTRACTION OF QUASI-PERIODIC SIGNALS

RELATED APPLICATION

This application claims the benefits of Canadian Application No. 2,524,507 filed Oct. 26, 2005.

FIELD OF THE INVENTION

This invention is related to the acquisition of signals, in particular, this invention is related to the acquisition of high-resolution quasi-periodic signals.

BACKGROUND OF THE INVENTION

A quasi-periodic signal with high signal-to-noise ratio, but low temporal resolution co-exists quite often with a related signal with low signal-to-noise ratio, but high temporal resolution. The quasi-periodic nature of the signal means that conventional correlation and spectral estimation techniques cannot be easily applied. One such example is the phonocardiogram and the related plethysmogram. Acquisition of accurate, high-resolution phonocardiogram is difficult because of motion artifacts, breathing, external noise, coughing and other transient disturbances of high magnitude. The various noise sources contribute to low signal-to-noise ratios for the phonocardiogram. At the same time, a plethysmogram provides a high signal-to-noise ratio but low temporal resolution heart-beat waveform.

Research into cardiac function, cardiac imaging, and other medical research requires the identification of a temporal reference point in the cardiac cycle. An area of interest in both cardiac research and cardiac imaging demands the processing of cardiac signals and images with high temporal resolution. The ability to acquire and register these signals and images with high resolution permits researchers and clinicians to use advanced techniques for extracting signals from noise to explore the microstructure of these signals as indicators of cardiac health.

The reference point used most frequently is the peak of the R-wave exhibited by the EKG. However, the EKG is a record of the electrical excitation of the heart and not a record of its mechanical activity. It is frequently the mechanical activity that is of interest for understanding heart murmurs and other heart sounds. Thus, use of the R-wave assumes that there is a constant relationship between the peak of the R-wave and the mechanical response of the heart. Further, use of the EKG requires electrical connections to the body requiring multiple wires, resulting in increase in complexity and preparation time.

Therefore, a temporal reference point with respect to the mechanical activity of the heart is preferred.

However, to date there have not been robust ways to identify a temporal reference point with sufficient resolution and precision for high-resolution detection, processing and reconstruction of quasi-periodic signals, including but not limited to electrical, pressure, and acoustic signals.

For example, heart sound information can be extracted from the phonocardiogram both for analysis and for training clinicians. In part this is because the phonocardiograph instrument used to acquire the phonocardiogram signal has the virtue of requiring only that the clinician hold a microphone to the chest of the patient, and in part because the phonocardiogram signal provides information to the clinician that is not easily available by other means.

However, analysis of the exemplary phonocardiogram is sometimes difficult because of motion artifacts, coughing, breathing, excessive body fat, variations in the position of the phonocardiograph microphone and background noise. The sounds that the clinician wants to hear are of very low amplitude and can be difficult to discern. These sounds can be indicators of significant cardiac conditions that influence treatment and management. In other words, the phonocardiogram signal tends to have a low signal-to-noise ratio.

As discussed before, the problem of phonocardiograph signal analysis is one example of problems one would face during the analysis and reconstruction of quasi-periodic signals with low signal-to-noise ratios but high temporal resolution that is co-existent with related signals with low signal-to-noise ratio, but high temporal resolution.

Therefore, quasi-periodic signal analysis, for example cardiac sound analysis, requires a means of differentiating artifacts from real signals. This is accomplished in many cases by averaging large numbers of heart sounds together through so-called "boxcar integration." Under the assumption that the differences between beats are due to noise, this technique averages together corresponding points in many beats, thereby building up a prototypical beat. Boxcar integration works well for periodic signals, as a temporal reference for each beat must be established with high accuracy. The quasi-periodicity of the heartbeat makes establishing this temporal reference difficult. Standard correlation techniques result in the loss of high frequency information in the signal. The techniques based on spectral estimation are also not appropriate.

Some attempts have been made to acquire and interpret quasi-periodic signals such as phonocardiogram.

U.S. Pat. No. 4,905,706 to Duff et al. describes a method and an apparatus for extracting information from acoustic heart signals and identifying coronary artery disease by recording and analyzing portion of the phonocardiogram lying between 100 to 600 Hz. An electrocardiogram is recorded and examined in order to pinpoint the diastolic window of PCG data. This window of data is subjected to autocorrelation analysis and spectral analysis, resulting in a partial correlation coefficient index and a power density index.

U.S. Pat. No. 5,109,863 to Semmlow et al., describes a method analyzing the diastolic heart sounds in order to identify a low level auditory component associated with turbulent blood flow in occluded coronary arteries. The diastolic heart sounds are modeled so that the presence of such an auditory component may be reliably indicated under high noise conditions. A method for automatically identifying and isolating a diastolic segment of a heart sound recording through a "window" placement technique is also described.

U.S. Pat. No. 5,159,932 to Zanetti et al. describes a method and apparatus for non-invasively monitoring the motion of a heart, to detect and display ischemia-induced variations in the heart's motion which indicate coronary artery disease.

U.S. Pat. No. 6,024,705 to Schlager et al. describes a computer-based automation for seismocardiographic waveform to produce a "number" for heart performance parameters, and particularly a positive-negative diagnosis of myocardial ischemia.

U.S. Pat. No. 6,572,560 to Watrous et al. teaches a method for extracting features from cardiac acoustic signals using a neural network. A wavelet is decomposed to extract time-frequency information, and identifying basic heart sounds using neural networks applied to the extracted time-frequency information.

U.S. Pat. No. 6,950,702 to Sweeney teaches a cardiac rhythm management system with a sensing circuit to sense a cardiac signal and a sensing processor to detect cardiac beats by utilizing certain morphological context of the sensed cardiac signal.

Prior art method and system, however, do not teach a method whereby two related quasi-periodic signals, one characterized by high signal-to-noise ratio, low temporal resolution and the other characterized by low signal-to-noise ratio, high temporal resolution, are used to acquire high-resolution quasi-periodic signals or to identify temporal reference points therein.

Therefore, there is a need for a novel method and system to find temporal reference points in quasi-periodic signals that indicate the same temporal point on each beat, so as to enable the use of available signal analysis methods.

SUMMARY OF THE INVENTION

The present invention uses a first quasi-periodic signal, characterized by high signal-to-noise ratio but low temporal resolution due to its low bandwidth, for example, an optical plethysmogram, and a second sensor to obtain a second quasi-periodic signal, characterized by a low signal-to-noise ratio but high temporal resolution, for example, a phonocardiogram, which together permit determining a set of consistent trigger points in the quasi-periodic signal that relate identically to the signal events that form the quasi-periodic signal, for example the sound events of the cardiac cycle, with high temporal resolution.

The present invention detects a feature of the second quasi-periodic signal that identifies a temporal region that straddles the heart sound. This region is then analyzed to find a consistent temporal trigger point with high resolution.

In accordance with one embodiment of the present invention there is provided a method for determining a plurality of temporal reference points within a quasi-periodic signal comprising the steps of: acquiring a first quasi-periodic signal, the first quasi-periodic signal having a low temporal resolution, and a high signal-to-noise ratio; acquiring a second quasi-periodic signal, the second quasi-periodic signal being related to the first quasi-periodic signal, and having a high temporal resolution and a low signal-to-noise ratio; determining a nominal interval of the first quasi-periodic signal by determining a most common frequency component of the first quasi-periodic signal; constructing and providing a shape filter for the first quasi-periodic signal using the nominal interval and slope crossings of the first quasi-periodic signal; forming a template for the first quasi-periodic signal; identifying reference time points for the first quasi-periodic signal by comparing the template with the first quasi-periodic signal; providing an envelope for the second quasi-periodic signal using the reference times; estimating reference points for the second quasi-periodic signal within the envelope; forming a second template for the second quasi-periodic signal; cross-correlating the second template with the second quasi-periodic signal around the reference points resulting in a highest correlation peak; and setting the reference points to the time of the highest correlation peak.

BRIEF DESCRIPTION OF DRAWINGS

The invention and the illustrated embodiments may be better understood, and the numerous objects, advantages, and features of the present invention and illustrated embodiments will become apparent to those skilled in the art by reference to the accompanying drawings. In the drawings, like reference numerals refer to like parts throughout the various views of the non-limiting and non-exhaustive embodiments of the present invention, and wherein:

FIG. 5(A)(B) illustrate the thresholds and the slope crossing; and

DETAILED DESCRIPTION

Reference will now be made in detail to some specific embodiments of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order to not unnecessarily obscure the present invention.

Reference throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

The term "quasi-periodic signal" is intended to describe a signal that is a sequence of representative signal portions, signal portions corrupted with noise and artifacts, and signal portions of varying lengths and values.

The term "trigger points" is intended to include temporal reference points that have arbitrary but identical relationships to the representative portions of the quasi-periodic signal.

The term "high temporal resolution" is intended to mean that the signal can be localized in time to within a very small range of times. Such signals may have high slope magnitudes so that the time at which the signal crosses a given, arbitrary threshold can be determined accurately and precisely. The term "low temporal resolution" is intended to mean that the signal cannot be localized in time to within a small range of times, but rather there is considerable uncertainty as to when the signal crosses the threshold.

The present invention provides a means of identifying a temporal reference point (or "trigger") in a quasi-periodic signal, for example, in the cardiac cycle, with high temporal resolution with respect to the wave pattern, for example that of a heart beat in a waveform with low signal-to-noise ratio, for example, the phonocardiogram provided by the phonocardiograph. The temporal reference points may then be used as the reference points for extraction of the wave pattern, for example, sound wave pattern of the heart with high temporal resolution and precision. The extraction may be achieved through, for example, but not limited to, "boxcar integration". Other suitable techniques may include triggered wavelet analysis and temporally triggered short-term spectral analysis.

Figure 1:
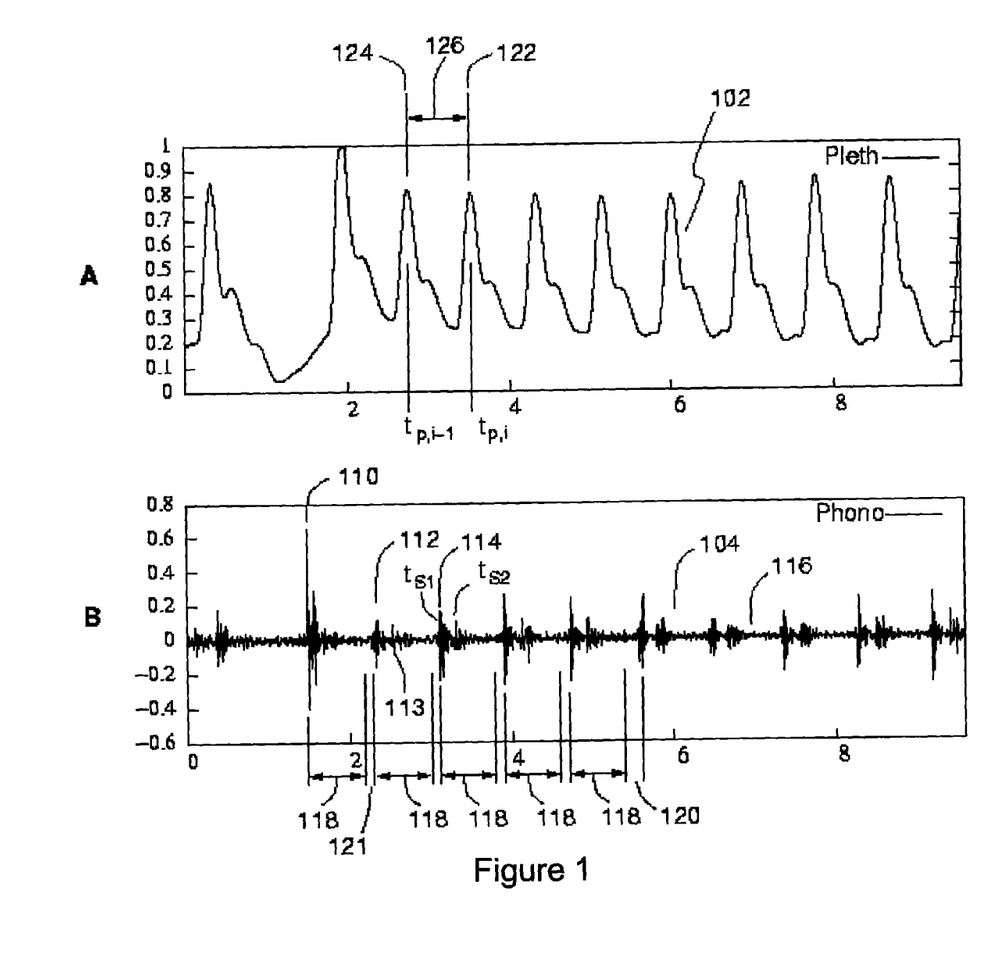
FIG. 1(A) illustrates an example of an optical plethysmogram.
FIG. 1(B) shows an example of a phonocardiogram signal.

Referring to FIG. 1, one embodiment of the present invention is illustrated using the example of a heart-beat waveform as a quasi-periodic signal. Since the heart sound 110, 112, 114 as measured by the phonocardiograph arises due to the mechanical motion of the heart, and since this motion repeats, then the waveform of the first heart sound may be considered to be identical for each subsequent heart beat.

The sounds of sequential heartbeats 110, 112, 114 as captured by the phonocardiograph are interfered by acoustic noise, motion artifacts, coughing and breathing, as well as electronic instrumentation and radio noise and electrical noise from machinery of all forms 116. As a result, each point in the phonocardiogram during each beat can be considered to have the value of that point $\Phi_i$ in a prototypical beat with noise $\zeta_i$ added to it, as follows:

$$\Phi_i = \tilde{\Phi}_i \zeta_i \qquad (1)$$

The noise sample $\zeta_i$ is considered to have two terms:

$$\zeta_i = \hat{\zeta}_i + \rho_i \qquad (2)$$

where the $\hat{\zeta}_i$, $\forall i$ are assumed to be independent, identically distributed samples of a zero-mean normal distribution, and the $\rho_i$ are samples taken from an unknown distribution that accounts for sporadic coughing, motions, gastro-intestinal motility, and other transient events.

In accordance with one embodiment of the present invention the $\Phi_i$ terms are extracted and both $\hat{\zeta}_i$ and $\rho_i$ are suppressed.

The phonocardiogram 104 can be considered to be a sequence of prototypical beat signals $\Phi$ with inter-beat interval $I_B$ in seconds, given by:

$$I_{B,j} = 60/H + v_j \qquad (3)$$

where $I_{B,j}$ is the duration of the j-th inter-beat interval, which is denoted as 118 in FIG. 1(B), H is the nominal heart rate in beats per minute and $v_j$ is a zero-mean random variable that captures the variation in the beat interval, an instance of which is denoted as 120, 121 in FIG. 1(B). The term $v_j$ makes the heartbeat quasi-periodic, unsuitable for spectral and correlation techniques.

In accordance with one embodiment of the present invention, a first, high signal-to-noise ratio and low temporal-resolution signal is used to identify locations in a second, low signal-to-noise ratio, high temporal resolution signal at which processing is to be performed to extract a high resolution temporal trigger. The signal may be quasi-periodic. Also referring to FIG. 2, a secondary sensor, for example, an optical plethysmograph sensor 202 may be used to identify the time intervals in which the heart beat occurs. Other examples of secondary sensors may include, but not be limited to, EKG, vertical motion accelerometer, force plate, static charge-sensitive bed, etc. The heart beat is first detected in the optical plethysmograph signal 102 using a two-step refinement process. The time of occurrence of these beats provides $t_{p,i}$, 122, a plethysmogram temporal reference point. The interval between $t_{p,i-1}$ 124 and $t_{p,i}$ 122 provides a "window" 126 in which to find the first two heart sounds, which are caused by the slamming of the mitral valve at the end of atrial systole and the slamming of the aortic valve near the end of ventricular systole, in the phonocardiogram 104.

The first two heart sounds 112, 113 are then isolated from the phonocardiogram 104. This is accomplished by first finding initial estimates of the times of these sounds $\tilde{t}_{S1,i}$ and $\tilde{t}_{S2,i}$ of the peaks of the phonocardiogram heart sound envelopes in the regions r defined by $t_{p,i-1}$ and $t_{p,i}$. The earlier of the two highest envelope peaks within each regions $r_i$ is deemed to be due to the first heart sound for that beat, with an initial estimate of its time of occurrence of $\tilde{t}_{S1,i}$.

The point-by-point inter-quartile average of the first heart sounds 110 is computed over a window of length equal to the previously determined inter-beat interval and centered on $\tilde{t}_{S1,i}$ to produce the initial $S_1$ prototype.

Finally, the high-resolution temporal reference point $t_{S1}$ is identified by finding the peak of a modified cross-correlation of the phonocardiogram with the initial $S_1$ prototype. Then the $S_1$ template $T_{S1}$ is generated by computing the point-by-point inter-quartile average using $t_{S1,i}$ for the time reference. The point-by-point inter-quartile standard deviation is also computed to provide a confidence measure for the template.

In one embodiment of the present invention, an optical plethysmograph 102 and a phonocardiograph 104 are used. The optical plethysmograph 102 captures the instantaneous blood density in peripheral tissue such as, but not limited to, the finger or the earlobe. As is well known in the art, the instantaneous blood density is pulsatile due to the beating of the heart. The resulting optical plethysmogram 102 exhibits the heartbeats with high signal-to-noise ratio but with low temporal resolution and with a significant time delay from ventricular systole of the heart beat.

Figure 2:
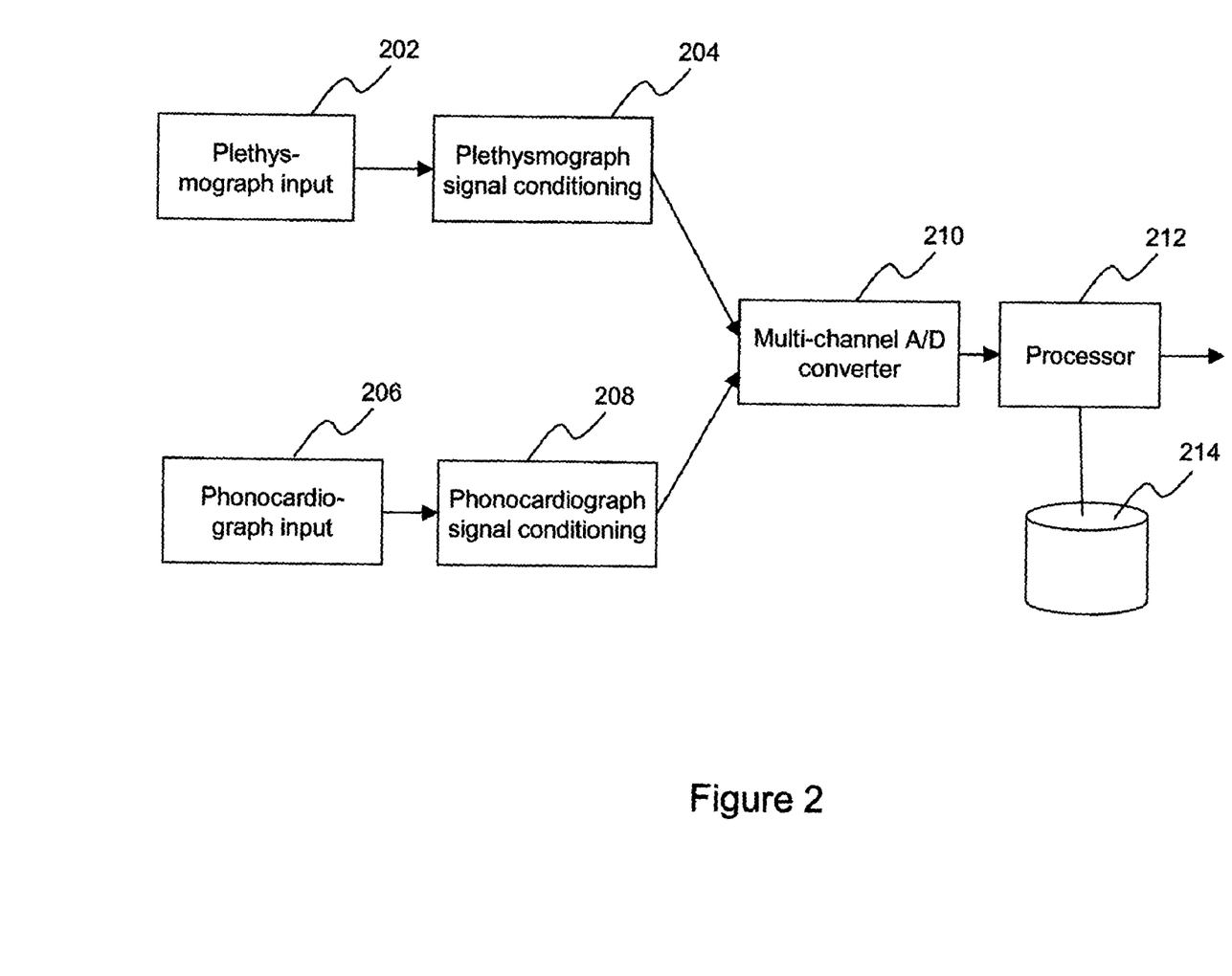
FIG. 2 is a example of a system in accordance with one embodiment of the present invention.

The phonocardiogram 104 is a record of the sounds made by the heart, as received by the phonocardiograph input 206. The phonocardiogram 104 typically has a low signal-to-noise ratio but the waveforms in it exhibit rapid changes of amplitude, thereby providing high temporal resolution.

In one embodiment, the present invention provides a means of combining the optical plethysmogram and phonocardiogram signals to produce a high-resolution, representative, heart-beat sound waveform with both high signal-to-noise ratio and high temporal resolution.

In one embodiment, the optical plethysmogram is acquired using a finger optical plethysmograph 202 connected to one channel of a multi-channel analog-to-digital (A/D) converter 210 via appropriate amplifiers and signal conditioning circuits 204. The phonocardiogram 102 is acquired using an acoustic sensor, for example, an electronic stethoscope 206, connected to a second channel of the A/D converter 210 via appropriate signal conditioning units 208. Signals from the optical plethysmograph 102 and the phonocardiograph 104 are acquired simultaneously from the multichannel A/D converter 210 by a processor 212. The data are acquired over a period of time and may be stored on the computer disc drive 214 for further processing.

In one embodiment of the present invention, the processing takes place upon completion of data collection. In another embodiment of the present invention, continuous collection and processing is contemplated. Other embodiments are contemplated in which processing is carried out by one or more dedicated or general purpose computational devices embedded with or integrated with the data acquisition devices. Yet other embodiments are contemplated in which the optical plethysmogram and the phonocardiogram are acquired using non-contact optical means such as cameras with appropriate, structured illumination for sensing motion and optical backscatter. Further embodiments are contemplated in which the first sensor includes but is not limited to a static charge sensitive bed, visual measurement of motion using Moiré interferometry or other visual technique, measuring disturbances in a localized electromagnetic field, capacitive sensing and other means to be contemplated.

Figure 3:
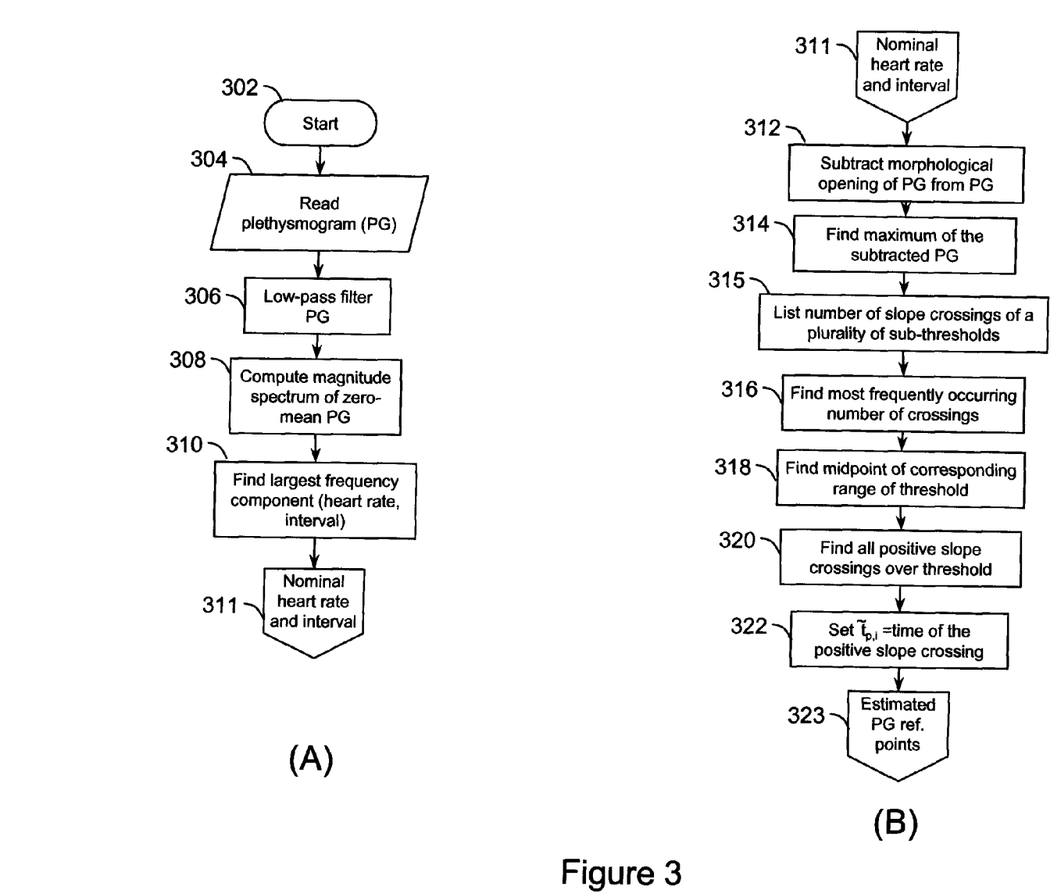
FIG. 3(A)-(E) show flowcharts in accordance with one embodiment of the present invention.

FIG. 3 illustrates an exemplary implementation to determine temporal reference points within a quasi-periodic signal in accordance with one embodiment of the present invention by using plethysmogram and phonocardiogram.

Referring to FIGS. 1-3, the plethysmogram (PG) 102 data may be read 304 from a storage media 214 or acquired from appropriate sensors. The plethysmogram 102 is low-pass filtered 306. The means of the plethysmogram is computed and subtracted from the plethysmogram. The resulting zero-mean plethysmogram in the time domain is transformed into the frequency domain using, for example, the Fast Fourier Transform 308. The frequency corresponding to the peak amplitude in the frequency domain is deemed to be the nominal heart rate 311.

Figure 4:
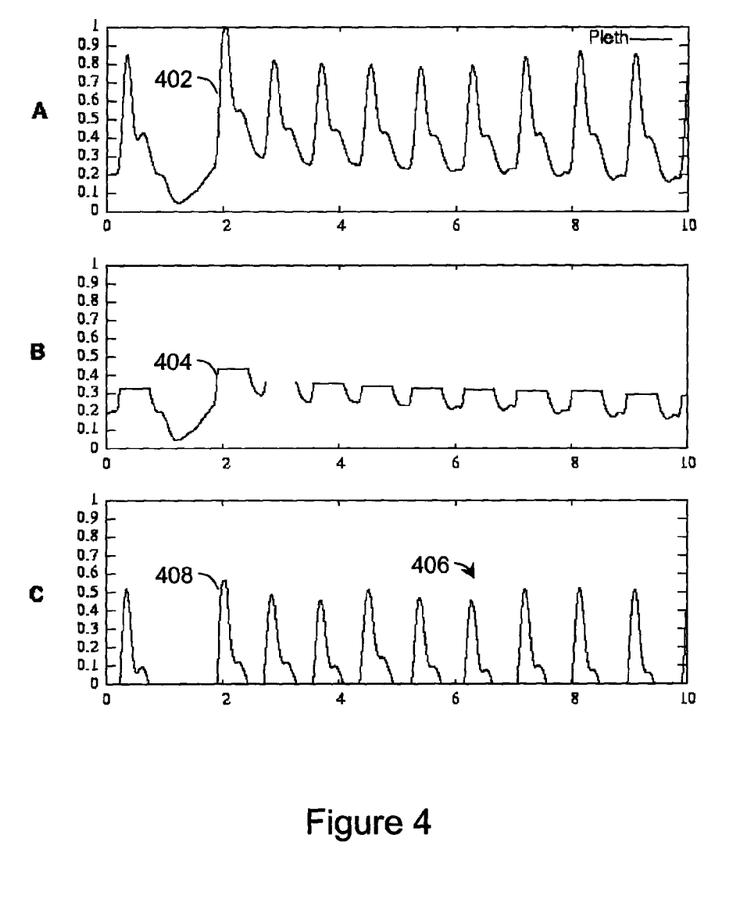
FIG. 4(A) illustrates a phonocardiogram.
FIG. 4(B) depicts a morphological opening of the phonocardiogram and FIG. 4(C) is a subtracted phonocardiogram.

Referring to FIG. 3(B), using the nominal heart rate and the corresponding nominal interval 311, a morphological opening of the plethysmogram is then computed. Morphological opening is an operation from the field of mathematical morphology. The morphological opening of a signal is a form of signal shape filter in which, for example, all of the signal is preserved except narrow regions of high amplitude such as signal peaks. The width of the region to be removed is determined by the size of the structuring element. The morphological opening of the plethysmogram is then subtracted from the plethysmogram 312. Referring to FIG. 4, a plethysmogram 402 is illustrated in FIG. 4(A), the morphological opening 404 in FIG. 4(B) employs a structuring element that is ½ the size of the inter-beat interval. The resultant subtracted plethysmogram 406 is illustrated in FIG. 4(C). The maximum value 408 of the result, after compensating for the baseline, is found 314.

Figure 5:
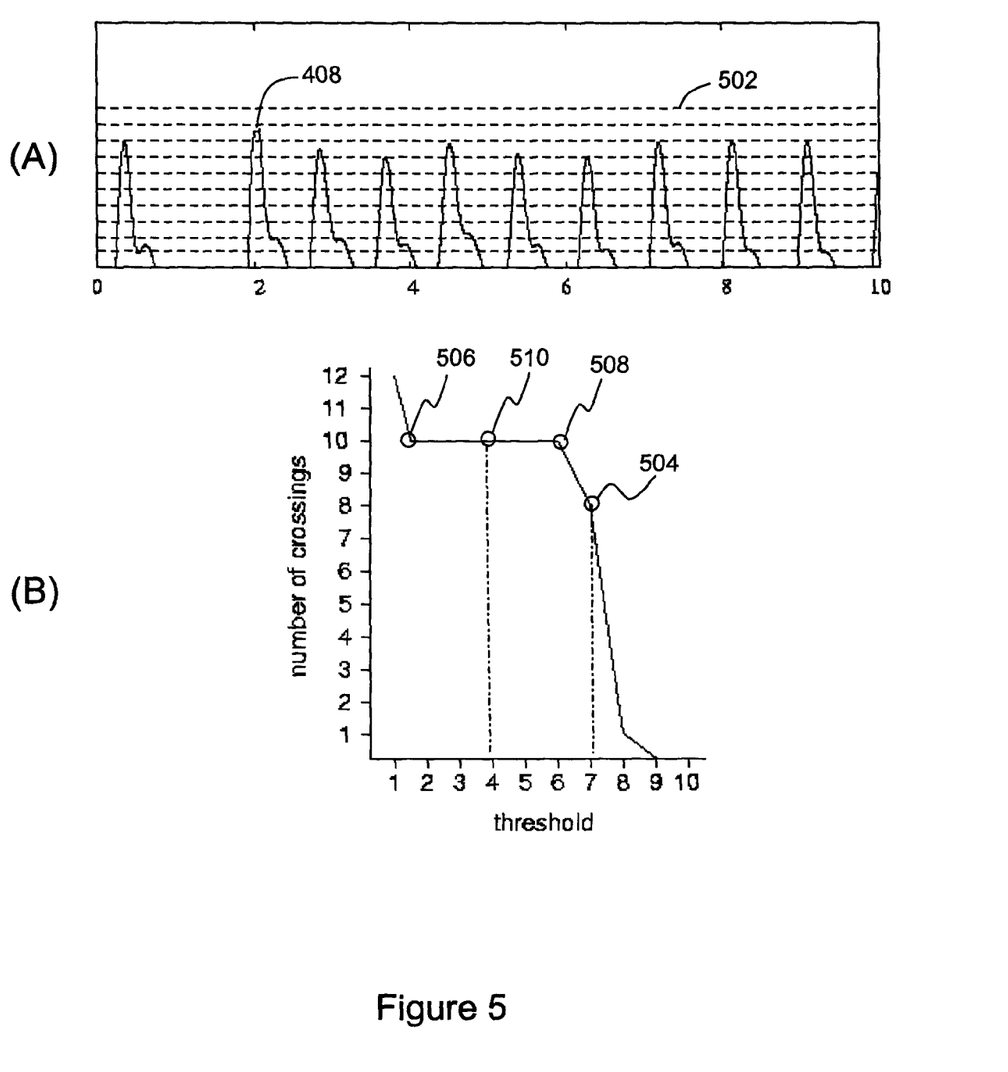

A plurality of thresholds, preferably equally spaced, is created spanning the range of baseline to the maximum value. The number of threshold crossings by those parts of the signal having a particular sign of slope, for example positive slope, for each threshold is created 315. Also referring to FIG. 5(A), ten thresholds 502 are shown. By traversing the threshold from left to right in the time axis, the number of the exemplary positive slope crossing can be counted, the result is illustrated in FIG. 5(B). For example, there are eight crossings for threshold 7, 504. The most frequently occurring number of positive-slope threshold crossings is found 316. In the example illustrated in FIG. 5, the most frequently occurring number of crossings is ten crossings 506, 508, corresponding to thresholds 2, 3, 4, 5, 6. The midpoint 510 of the range of consecutive threshold values having this number of threshold crossings is found 318, which in the example is threshold 4. The plethysmogram is then compared with this threshold wherein the time $\tilde{t}_{p,i}$ of the positive-slope crossing 320 of this threshold is recorded for each of the crossings i 322.

Referring to FIG. 3(C), the estimated plethysmogram temporal reference point $\tilde{t}_{p,i}$ 323 is then refined to generate more accurate reference points $t_{p,i}$. A robust estimate, for example, an inter-quartile mean, of the plethysmogram template $P_T$ is computed using the inter-quartile mean 324.

To compute the inter-quartile mean, a window w of length $\Delta t = 60/H \times 1000$ samples is centered on each $t_{p,i}$ for all i. Then, for each j, j=1 ... $\Delta t$, a sorted list L of the plethysmogram values $Pt_{p,i-(\Delta t)/2+j} \forall_i < n$ is created and sorted in ascending order, where n is the number of heart beats. The mean of the $L_k$, n/4≦k≦3n/4 points is computed and the plethysmogram template at point j, $P_{T,j}$, is set equal to this value.

The plethysmograph temporal reference points $t_{p,i}$, i∈ 329 is computed from $\tilde{t}_{p,i}$ by cross-correlating P with $P_T$ 326 and finding the peaks of the correlation within the windows w centered on the $\tilde{t}_{p,i}$ 328.

Referring to FIG. 3 (D), the phonocardiogram 104 is read 303. The phonocardiogram 104 is low-pass filtered 305. A simple envelope of the phonocardiogram signal S is computed 330. Starting at the first peak 332, the two largest phonocardiogram envelope peaks 334 within the interval $t_{p,i}$ and $t_{p,i+1}$ with i=1 are identified. The first of these peaks is taken to be due to the first heart sound, $S_1$, and the second is taken to be due to the second heart sound, $S_2$. The sample number $\tilde{t}_{S1,i}$ is recorded as the estimate of the time of occurrence of $S_1$, 334. Repeat for 1≦i≦n 338. The result is a list of the estimated times of the first heart sound for each beat 341.

The estimates $\tilde{t}_{S1,i}$ is then refined to produce the phonocardiogram temporal reference points $t_{s1,i}$, $\forall$i≦n.

Referring to FIG. 3(E), a robust initial template $\tilde{S}_T$ of the first heart sound is produced from the phonocardiogram in windows w of width $\Delta t$ that are centered on the estimated phonocardiogram temporal reference points $\tilde{t}_{S1,i}$ in a manner similar to that used to compute the plethysmogram template $P_T$ 342. The phonocardiogram and the phonocardiogram initial template $\tilde{S}_T$ are clipped to empirically determine minimum and maximum values 344. The clipped $\tilde{S}_T$ is cross-correlated with the clipped phonocardiogram and the result is filtered with a low-pass filter 346. By clipping the waveform the result of the cross-correlation is sensitive to the location of the signal transitions, and not to the magnitude of the signals. Starting at the first peak 348, the highest value of the correlation is sought on the intervals defined by the estimated phonocardiogram temporal reference points as $[\tilde{t}_{S1,i}, \tilde{t}_{S1,i1}]$ $\forall$1≦i≦n 350. The times at which these peaks occur are the phonocardiogram temporal reference points $t_{s1,i}$ that are sought 352. All intervals are repeated until data are exhausted 354.

The template $S_T$ of the prototypical phonocardiogram s1 heart sound that is sought is then created. For each temporal reference point $t_{s1,i}$, i=1 ... n−1, the inter-quartile mean and inter-quartile standard deviation are computed in a manner similar to that used to compute the $P_T$ 358, the robust estimate of the plethysmograph signal. The mean and the standard deviation are stored on the computer hard disc in the current embodiment 360.

Figure 6:
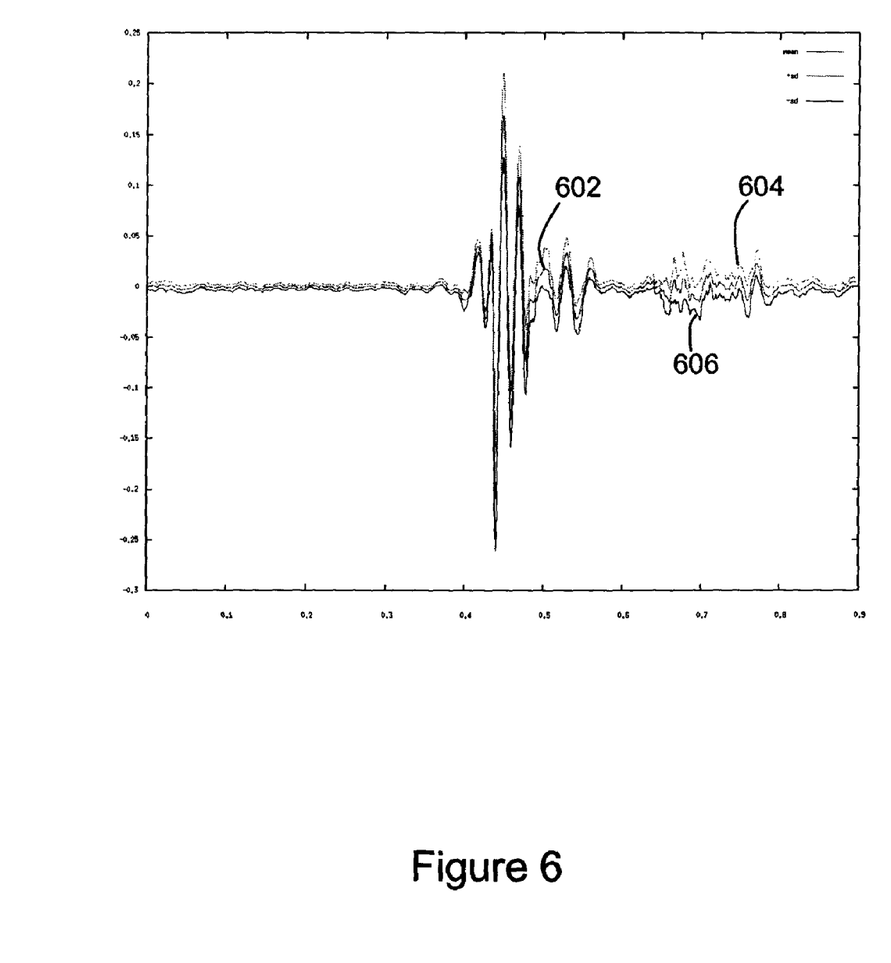
FIG. 6 depicts high resolution template $Ts_1$ of the first heart sound.

The result is shown in FIG. 6, wherein the mean of the phonocardiogram, shown by the middle curve 602, denotes the template of the prototypical phonocardiogram $S_1$ heart sound. The upper curve 604 denotes the mean plus one standard deviation and the lower curve 606 denotes the mean minus one standard deviation.

While particular embodiments of the present invention have been shown and described, changes and modifications may be made to such embodiments without departing from the true scope of the invention. A non-limiting example of the present invention may be an independent variable which is not time dependent. Other examples may include, but are not limited to other medical and health related signals such as electrocardiogram and breath-sound signals.

What is claimed is:

1. A method for determining a plurality of temporal reference points within a quasi-periodic signal comprising the steps of:
   acquiring (304) a first quasi-periodic signal, the first quasi-periodic signal having a low temporal resolution, and a high signal-to-noise ratio;
   acquiring a second quasi-periodic signal, the second quasi-periodic signal being related to the first quasi-periodic signal, and having a high temporal resolution, and a low signal-to-noise ratio;
   determining (310) a nominal interval of the first quasi-periodic signal by determining a most common frequency component of the first quasi-periodic signal;
   constructing and providing (312) a shape filter for the first quasi-periodic signal using the nominal interval for determining (320) slope crossings;
   forming (324) a template for the first quasi-periodic signal;
   identifying (328) reference time points for the first quasi-periodic signal by comparing the template with the first quasi-periodic signal;
   providing (330) an envelope for the second quasi-periodic signal using the reference times;
   estimating (336) reference points for the second quasi-periodic signal within the envelope;
   forming (342) a second template for the second quasi-periodic signal;
   cross-correlating (346) the second template with the second quasi-periodic signal around the reference points resulting in a highest correlation peak (350); and
   setting (352) the reference points to the time of the highest correlation peak.

2. The method according to claim 1, wherein the first quasi-periodic signal is a first heart-beat waveform, and the second quasi-periodic signal is a second heart-beat waveform.

3. The method according to claim 2, wherein the second heart beat waveform is a phonocardiogram.

4. The method according to claim 2, wherein the first heart beat waveform is a plethysmogram having a plurality of blood-density pulses.

5. The method according to claim 1, wherein the step of determining a nominal beat rate further comprises the steps of:
   low-pass-filtering (306) the first quasi-periodic signal; and
   determining (310) the largest frequency component in a frequency domain after a Fourier transform of the low-pass-filtered first quasi-periodic signal.

6. The method according to claim 1, wherein the shape filter for identifying signal events of interest is a morphological opening.

7. The method according to claim 6, wherein the step of providing a threshold further comprises the steps of:
   subtracting (312) the morphological opening of the first quasi-periodic signal from the first quasi-periodic signal;
   determining (314) a maximum for the subtracted first quasi-periodic signal;
   providing a plurality of sub-thresholds between a baseline and the maximum;
   determining (316) slope-crossings for each of the plurality of sub-thresholds resulting in a group of sub-thresholds, each of the group of sub-thresholds having identical number of crossings;
   determining (318) a midpoint of the sub-thresholds, and providing the midpoint as the threshold.

8. The method according to claim 7, wherein the sub-thresholds are equal spaced.

9. The method according to claim 1, wherein the step of identifying reference time points further comprises the step of:
   cross-correlating (326) the first template with the first quasi-periodic signal to identify the reference time points.

10. The method according to claim 1, wherein the step of estimating reference points further comprises the steps of:
    determining (334) two largest peaks in the interval for the second quasi-periodic signal; and
    setting (336) a reference point to the time of the occurrence of the first of the two largest peaks.

11. The method according to claim 1, wherein the step of cross-correlating further comprises the step of clipping (344) the second template and the second quasi-periodic signal.

12. The method according to claim 1, wherein the slope crossing is positive slope crossing.

13. The method of claim 1 wherein the first quasi-periodic signal or the second quasi-periodic signal is stored in data storage and acquired therefrom.

14. The method of claim 1 wherein the first quasi-periodic signal or the second quasi-periodic signal is provided remotely.

15. A system for determining a plurality of temporal reference points within a quasi-periodic signal comprising:
    means for acquiring a first quasi-periodic signal, the first quasi-periodic signal having a low temporal resolution, and a high signal-to-noise ratio;
    means for acquiring a second quasi-periodic signal, the second quasi-periodic signal being related to the first quasi-periodic signal, and having a high temporal resolution, and a low signal-to-noise ratio;
    means for determining a nominal interval of the first quasi-periodic signal by determining a most common frequency component of the first quasi-periodic signal;
    means for constructing and providing a shape filter for the first quasi-periodic signal using the nominal interval for determining slope crossings;
    means for forming a template for the first quasi-periodic signal;
    means for identifying reference time points for the first quasi-periodic signal by comparing the template with the first quasi-periodic signal;
    means for providing an envelope for the second quasi-periodic signal using the reference times;
    means for estimating reference points for the second quasi-periodic signal within the envelope;
    means for forming a second template for the second quasi-periodic signal;
    means for cross-correlating the second template with the second quasi-periodic signal around the reference points resulting in a highest correlation peak; and
    means for setting the reference points to the time of the highest correlation peak.

16. A storage medium readable by a computer encoding a computer program for execution by the computer to carry out a method for determining a plurality of temporal reference points within a quasi-periodic signal, the computer program comprising:
    code means for acquiring a first quasi-periodic signal, the first quasi-periodic signal having a low temporal resolution, and a high signal-to-noise ratio;

code means for acquiring a second quasi-periodic signal, the second quasi-periodic signal being related to the first quasi-periodic signal, and having a high temporal resolution, and a low signal-to-noise ratio;

code means for determining a nominal interval of the first quasi-periodic signal by determining a most common frequency component of the first quasi-periodic signal;

code means for constructing and providing a shape filter of the first quasi-periodic signal using the nominal interval for determining slope crossings;

code means for forming a template for the first quasi-periodic signal;

code means for identifying reference time points for the first quasi-periodic signal by comparing the template with the first quasi-periodic signal;

code means for providing an envelope for the second quasi-periodic signal using the reference times;

code means for estimating reference points for the second quasi-periodic signal within the envelope;

code means for forming a second template for the second quasi-periodic signal;

code means for cross-correlating the second template with the second quasi-periodic signal around the reference points resulting in a highest correlation peak; and code means for setting the reference points to the time of the highest correlation peak.

17. A method for providing a high-resolution template for a quasi-periodic signal comprising the steps of:

acquiring (304) a first quasi-periodic signal, the first quasi-periodic signal having a low temporal resolution, and a high signal-to-noise ratio;

acquiring a second quasi-periodic signal, the second quasi-periodic signal being related to the first quasi-periodic signal, and having a high temporal resolution, and a low signal-to-noise ratio;

determining (310) a nominal interval of the first quasi-periodic signal by determining a most common frequency component of the first quasi-periodic signal;

constructing and providing (312) a shape filter for the first quasi-periodic signal using the nominal interval for determining (320) slope crossings;

forming (324) a template for the first quasi-periodic signal;

identifying (328) reference time points for the first quasi-periodic signal by comparing the template with the first quasi-periodic signal;

providing (330) an envelope for the second quasi-periodic signal using the reference times;

estimating (336) reference points for the second quasi-periodic signal within the envelope; and forming (342) a second template for the second quasi-periodic signal.

\* \* \* \* \*